US011141198B2

(12) United States Patent
Van De Sande et al.

(10) Patent No.: US 11,141,198 B2
(45) Date of Patent: Oct. 12, 2021

(54) COUPLING DEVICE FOR IN AN ORTHOPAEDIC SYSTEM

(71) Applicant: UMC UTRECHT HOLDING B.V., Zeist (NL)

(72) Inventors: Barbara Johanna Stefanie Van De Sande, Amsterdam (NL); Ralph Johan Bernhard Sakkers, Loenen aan de Vecht (NL); Lucas Alphonsus Maria Evers, Zeist (NL)

(73) Assignee: UMC Utrecht Holding B.V.

( * ) Notice: Subject to any disclaimer, the term of this patent is extended or adjusted under 35 U.S.C. 154(b) by 179 days.

(21) Appl. No.: 15/566,315

(22) PCT Filed: Apr. 14, 2016

(86) PCT No.: PCT/EP2016/058258
§ 371 (c)(1),
(2) Date: Oct. 13, 2017

(87) PCT Pub. No.: WO2016/166236
PCT Pub. Date: Oct. 20, 2016

(65) Prior Publication Data
US 2018/0098791 A1 Apr. 12, 2018

(30) Foreign Application Priority Data
Apr. 15, 2015 (WO) ................. PCT/EP2015/058195

(51) Int. Cl.
*A61B 17/64* (2006.01)
*A61B 17/62* (2006.01)
(52) U.S. Cl.
CPC .......... *A61B 17/6458* (2013.01); *A61B 17/62* (2013.01)

(58) Field of Classification Search
CPC ................................. A61B 17/60–66
See application file for complete search history.

(56) References Cited

U.S. PATENT DOCUMENTS 2,391,537 A * 12/1945 Anderson ............. A61B 17/66
606/59
3,727,610 A * 4/1973 Riniker ............. A61B 17/6441
606/56
3,993,055 A * 11/1976 Volkov ............... A61B 17/6441
606/90

(Continued)

FOREIGN PATENT DOCUMENTS

GB 2040168 A 8/1980
WO WO2008/147179 A1 12/2008
WO WO2010/029412 A2 3/2010

OTHER PUBLICATIONS

International Preliminary Report on Patentability dated Oct. 17, 2017; (PCT/EP2016/058258); 8 pages.

*Primary Examiner* — Lynnsy M Summitt
(74) *Attorney, Agent, or Firm* — Akerman LLP (57) ABSTRACT

Coupling device for connecting an annular fixation member to a bone pin, wherein the coupling device comprises pin connecting means arranged for connecting the bone pin to the coupling device and ring connecting means arranged for removably connecting the annular fixation member to the coupling device, wherein the coupling device further comprises fixator connecting means arranged for removably connecting a fixator to the coupling device, wherein the ring connecting means and the fixator connecting means are arranged for simultaneously connecting the annular fixation member and the fixator while the pin connecting means are connected to the bone pin.

14 Claims, 4 Drawing Sheets

(56) References Cited

U.S. PATENT DOCUMENTS

| | | | | |
|---|---|---|---|---|
| 4,365,624 A * | 12/1982 | Jaquet | A61B 17/6441 | 606/56 |
| 4,624,249 A * | 11/1986 | Alvarez Cambras | A61B 17/6441 | 606/54 |
| 5,087,258 A * | 2/1992 | Schewior | A61B 17/62 | 606/56 |
| 5,797,908 A * | 8/1998 | Meyers | A61B 17/6483 | 606/54 |
| 5,885,282 A * | 3/1999 | Szabo | A61B 17/62 | 606/56 |
| 6,428,540 B1 * | 8/2002 | Claes | A61B 17/66 | 606/53 |
| 6,616,664 B2 * | 9/2003 | Walulik | A61B 17/645 | 600/230 |
| 6,860,883 B2 * | 3/2005 | Janowski | A61B 17/645 | 606/56 |
| 7,422,593 B2 * | 9/2008 | Cresina | A61B 17/66 | 606/54 |
| 7,749,224 B2 * | 7/2010 | Cresina | A61B 17/6425 | 606/54 |
| 8,388,625 B2 * | 3/2013 | Bagnasco | A61B 17/62 | 606/57 |
| 8,419,733 B2 * | 4/2013 | Hajianpour | A61B 17/62 | 606/54 |
| 9,393,045 B2 * | 7/2016 | Cresina | A61B 17/645 | |
| 9,554,837 B2 * | 1/2017 | Schonhardt | A61B 17/8047 | |
| 10,390,859 B2 * | 8/2019 | Sakkers | A61B 17/62 | |
| 2003/0181911 A1 * | 9/2003 | Venturini | A61B 17/6466 | 606/56 |
| 2006/0155276 A1 * | 7/2006 | Walulik | A61B 17/6416 | 606/59 |
| 2010/0191239 A1 * | 7/2010 | Sakkers | A61B 17/62 | 606/59 |
| 2011/0082458 A1 | 4/2011 | Crozet et al. | | |
| 2017/0215922 A1 * | 8/2017 | De Oto | A61B 17/62 | |

* cited by examiner

COUPLING DEVICE FOR IN AN ORTHOPAEDIC SYSTEM

The present invention relates to a coupling device for connecting an annular fixation member to a bone pin, wherein the coupling device comprises pin connecting means arranged for connecting the bone pin to the coupling device and ring connecting means arranged for connecting the annular fixation member to the coupling device.

Such a device is for instance known from international publication WO 2008/147179 A1.

In this publication, a system for correcting bones is described. In this system, at least one first pin which can be connected to the bone at a first location and at least a second pin which can be connected to the bone at a second location at a distance from the first location are provided.

During a correction phase for adjusting the bone between the first and second pins, two annular or ring shaped fixation members are connected to bone pins at either side of a bone region to be corrected using coupling devices. These coupling devices are arranged to connect to at least one pin, typically a plurality of bone pins, on the one hand and to connect to the ring shaped members on the other hand. Means for adjusting the mutual distance and orientation of the annular fixation members are arranged between the annular fixation members. These means for instance comprise a plurality of telescopic tubes for adjusting and setting the mutual distance and orientation of the annular fixation members. In a hardening phase, wherein the relatively flexible bone in the correction phase is hardened, the mutual orientation between the pins is maintained by a unilateral fixator, such that the ring shaped members can be removed. This results in a more compact system during the hardening phase.

It is a goal, amongst other goals, of the present invention to provide an improved and/or more efficient coupling device, in particular for use in a system for correcting bones as described above.

In order to meet this goal, amongst other goals, the coupling device according to the preamble is characterized in that the coupling device further comprises fixator connecting means arranged for connecting a fixator to the coupling device, wherein the ring connecting means and the fixator connecting means are arranged for simultaneously connecting the annular fixation member and the fixator while the pin connecting means are connected to the bone pin. According to the invention, the coupling device is arranged to connect, i.e. is connectable, to the bone pin, the annular fixation member and a fixator, for instance a unilateral fixator, at the same time. The coupling device is thereto provided with respective connecting means, or connectors, to connect to a bone pin, an annular fixation member and the fixator. This reduces the number of parts of the system for correcting bones and allows an efficient transition from the correction phase to the hardening phase.

More specifically, in the correction phase as mentioned above, use is made of the annular fixation member, preferably one at either side of the bone region to be corrected, whereas in the hardening phase, use is made of a fixator arranged between the bone pins at either sides of the bone region to be corrected. Using the coupling device according to the invention, the fixator can be coupled to the same coupling device as to which the annular fixation member is connected, such that the annular fixation member can be efficiently exchanged with the fixator, for instance a unilateral fixator. The ring connecting means are therefore preferably arranged to removably connect the annular fixation member to the coupling device.

In order not to reduce the tension between the bone pins inserted at either side of the bone region to be corrected, it is of importance that the annular fixation member and the fixator can be coupled in a load bearing manner to the coupling device at the same time and preferably also each separately. Also the fixator connecting means are therefore preferably arranged to removably connect the fixator to the coupling device. The ring connecting means and the fixator connecting means are further preferably sufficiently separated on the coupling device such that the annular fixation member can be removed from the coupling device while the fixator is connected to the coupling device and vice versa. This enables removal of the annular fixation member in the hardening phase while the fixator acts as load bearing structure between the bone pins at either side of the bone region to be corrected. On the other hand, during the correction phase, the fixator does not need to be connected or can be flexibly coupled to the coupling devices between the bone pins on either side of the bone region to be connected.

As mentioned, the fixator is preferably a unilateral fixator and is arranged to be coupled to two coupling devices, each connected to at least one bone pin at either side of the bone region to be corrected. Typically, such a fixator is provided with a lockable ball joint such that the fixator can be moved between a fixed position, in which the fixator is rigidly connected between the end parts connectable to the coupling devices, and a flexible position, in which said end parts are moveable with respect to each other.

The annular fixation member and the fixator are both connectable to the coupling device such that both the annular fixation member and the fixator are connectable to the bone pin using the same pin connecting means. In other words, although the coupling need not to be a monolithic piece, and can comprise several parts as will be explained in greater detail below, the annular fixation member and the fixator are connectable to the coupling device preferably not via a bone pin.

In order to allow an efficient correction, it is preferred if in connected state, the annular fixation member, and preferably also the fixator, are arranged spatially between the bone pins on either side of the bone region, seen along the longitudinal axis of the bone to be corrected. According to this configuration, the coupling device can be connected to the bone pins at either side of the bone region to be corrected with the bone pins being located outwardly, i.e. enclosing the annular fixation member and preferably also the fixator seen along the longitudinal axis of the bone to be corrected. At the proximal side, i.e. the proximal coupling device, the bone pin thus extends proximally to the annular fixation means, at the distal coupling device the bone pin extends distally from the annular fixation means. The bone pins hereby do not interfere with any correction means arranged between the annular fixation members in the correction phase.

The bone pin connecting means are therefore preferably arranged to connect to at least one bone pin at a first position on the coupling device, wherein the ring connecting means are arranged to connect to an annular fixation member on a second position, wherein the first and second positions are different. The positions are different along a longitudinal axis of the coupling device, which typically corresponds to the longitudinal axis of the bone to be corrected. Therefore, according to a preferred embodiment, the bone pin connecting means are arranged near, preferably at, a first end of the coupling device, wherein the ring connecting means are arranged towards the opposite end of the coupling device.

It is further preferred if also the fixator is arranged spatially between the bone pins in connected state. The bone pin connecting means are therefore preferably arranged to connect to at least one bone pin at a first position towards a first end of the coupling device and wherein the ring connecting means and the fixator connecting means are arranged to connect the annular fixation member, respectively the fixator, at positions towards the opposite end of the coupling device. Both the annular fixation member and the fixator are according to this embodiment connected to the other end of the coupling body to which the bone pins are connected. An efficient and compact embodiment is hereby obtained if the bone pin connecting means are arranged towards the first end of the coupling device and wherein the ring connecting means and the fixator connecting means are arranged towards the opposite end of the coupling device.

An efficient connection between the fixator and the coupling device is obtained if according to a further preferred embodiment the bone pin connecting means are arranged to connect to at least one bone pin at a first end of the coupling device and wherein the fixator coupling means are arranged at the opposite second end. The ring connecting means are then preferably arranged between the pin connecting means and the fixator connecting means.

The fixator connecting means are arranged to preferably removably couple a fixator, for instance a unilateral fixator as mentioned above. Coupling devices which are connectable to a fixator as such are known and the connecting means typically include a releasable connection in the form of a clamping, clicking or snapping connection, for instance a bayonet connection between an end part of the fixator and an end of the coupling device.

The pin connecting means preferably comprise at least one hole for receiving a bone pin. Preferably, the coupling device is arranged to connect to a plurality of bone pins. Typically, these bone pins are inserted into the bone along a line, wherein the bone pins are received in correspondingly orientated holes in the coupling device. The pin connecting means hereby comprise a plurality of holes.

It is however also possible that the pin connecting means are arranged to receive and connect non-parallel extending bone pins. The pin connecting means are then provided with correspondingly shaped and orientated means for receiving and connecting said pins. This may for instance be the case for bone pins not extending through the centre of the bone, which also engage and pass through the outer stiffer parts of the bone, i.e. the compact bone.

However, an efficient connection between a bone pin, and preferably a plurality of bone pins, is obtained if according to further preferred embodiment the pin connecting means comprise a first clamping body part and a second clamping body part arranged for clamping at least one bone pin there between. The parts are preferably provided with cooperating locking means, for instance in the form of a locking screw, for interlocking the two body parts together to clamp and lock the bone pin between the bodies. Even more preferably, the body parts are provided with cooperating recesses which in connected state are arranged to closely receive a pin.

According to a further preferred embodiment, the coupling device has a substantially cylindrical body which is formed by two semi cylinders in the form of the clamping body parts. In other words, the two clamping body parts preferably together form an at least substantially cylindrical coupling device in the connected state.

According to a further preferred embodiment, the ring connecting means are arranged to connect an annular fixation member to a side surface of the coupling device. This allows an efficient connection. It is further advantageously that connecting the annular fixation member to a side surface of the coupling device, for instance the coupling device having the cylindrical shape as mentioned above, allows locating the fixator connecting means on an end surface of the coupling device. As mentioned above, preferably the other end of the coupling device is then provided with the pin connecting means, for instance in the form of the recesses on the semi cylindrical clamping bodies as mentioned above.

According to a further preferred embodiment, the ring connecting means comprise a groove receiving the annular fixation member. This results in a compact configuration, as the annular member may be connected close to, in fact at least partially countersunk, in the coupling device. When the annular fixation member is received at least partially countersunk in the groove, movement between annular fixation member and the coupling device is already limited. The height of the groove thereto preferably corresponds to the height of the annular fixation member.

The bone connecting means are preferably arranged to receive the pin along a pin connecting axis, wherein the groove is preferably arranged in the coupling device at least along the perimeter intersecting, in projection, the pin connecting axis. The groove is located at a position opposite the bone in connected state, such that the annular fixation member can be connected at a radial outwardly location, seen with respect to the longitudinal axis of the bone. This allows easy removal of the annular fixation member, while the groove allows a compact configuration.

An efficient connection is obtained if the ring connecting means comprise a connecting surface extending in a plane parallel to the plane of the annular fixation member to be connected, wherein the connecting surface is provided with connecting holes which are arranged to connect to holes of the annular fixation member. The surface, for instance in form of a flange, may for instance protrude from a side surface of the coupling device, thereby allowing a connection of the fixator near and end of the coupling device.

The connecting holes in the connecting surface are preferably located in accordance with the locations of the holes in the annular member. The annular fixation member can then be connected to the connecting surface using suitable screws. This allows an efficient and reliable connection between the coupling device and the annular fixation member using the already present holes of the annular member. In particular in case the annular member is to be connected to a side surface of the coupling device as mentioned above, this provides a reliable connection.

Although it is conceivable that the annular fixation member is directly coupled to the body of coupling device, for instance to the connecting surface thereof as mentioned above, it is preferred if according to a further preferred embodiment the ring connecting means comprise a connecting profile provided with connecting holes which are arranged to connect to connection holes of the annular fixation member, wherein the connecting profile is further provided with connection means for connecting the connecting profile to the coupling device. The connecting profile is preferably removably coupled to the coupling device, such that also the connecting profile can be removed from the coupling device when the annular fixation member is removed. This results in a compact configuration in the hardening phase.

A reliable connection between the coupling device and the connecting profile is obtained if the groove for receiving the annular fixation member is arranged for receiving the connecting profile. The groove is then shaped to receive the connecting profile in connection with the annular fixation member.

To allow an efficient connection, the connecting profile preferably comprises the first surface extending in a first plane parallel to the plane of the annular fixation member to be connected. The connecting profile preferably further comprises a second surface under an angle, preferably substantially extending substantially orthogonally, with respect to the connecting surface, wherein the second surface is provided with the connection means for connecting the connecting profile to the coupling device. This allows connecting the connecting profile to the coupling device in a correction direction under an angle, preferably substantially orthogonally, with respect to the connection direction of the connecting profile to the annular fixation member. Preferably, the connection means for connecting the connecting profile to the coupling device are arranged to engage in the groove for receiving the connecting profile as mentioned above.

According to a further preferred embodiment, the connecting profile has a substantially U-shaped cross-section, wherein the legs of the U-shape are shaped to closely receive the annular fixation member there between and wherein the connection means for connecting the connecting profile to the coupling device are provided in the base of the U-shape. Preferably both legs of the U-shape are provided with holes coinciding with a hole of the annular fixation member, such that a reliable connection is obtained between the connection profile and the annular fixation member. The base of the U-shape, a surface orthogonally to the legs of the U-shape is then provided with connecting means for connection with the coupling device, for instance in the groove thereof.

The connection means for connecting the connecting profile to the coupling device preferably comprise at least one hole, wherein the coupling device is provided with a coinciding hole for receiving a screw therein. The holes hereby preferably have an orientation under an angle, preferably extending substantially orthogonally, with respect to the orientation of the holes in the annular fixation member.

According to a specific preferred embodiment wherein the pin connecting means are formed by two clamping bodies for receiving a pin there between, the connection profile is arranged to be connected to both clamping bodies. The connecting profile is thereto preferably provided with at least two holes for cooperating with at least one hole of each of the clamping bodies. Specifically, the connection means preferably comprise a first pair of coinciding holes in the connecting profile and the first clamping body and a second pair of coinciding holes in the connecting profile and the second clamping body. Also the connecting profile can hereby function as a lock for locking the clamping bodies together.

In order to allow compensation for different types of bone pins or minor varieties in their orientation, it is preferred if at least one of the holes is slot shaped. This provides some movement in the longitudinal direction of the slot. The slot preferably has a width extending in the clamping direction of the two clamping bodies.

The invention further relates to a system for correcting bones provided with at least one coupling device according to the invention. Specifically, the invention further relates to a System for correcting bones, comprising:

at least a first pin which can be connected to the bone at a first location;
at least a second pin which can be connected to the bone at a second location at a distance from the first location;
at least one coupling device according to the invention coupled to at least the first pin;
a fixator which is coupled removably to the coupling device and the second pin for the purpose of fixing the mutual distance between the pins during a hardening phase; and
at least a first annular fixation member which is removably coupled to the coupling device and at least a second annular fixation member which is removably connected to the second pin for the purpose of adjusting the bone during the correction phase while the fixator is connected between the two pins.

Preferably the system is provided with two coupling devices according to the invention at either side of the bone region to be corrected. Specifically, the system preferable comprising a second coupling device coupled to the second pin, wherein the fixator which is coupled removably to the two coupling devices for the purpose of fixing the mutual distance between the pins during the hardening phase, and wherein the second annular fixation member is removably connected to the second coupling device for the purpose of adjusting the bone during the correction phase.

It is then preferred as mentioned above if the pin connecting means are arranged outwardly with the respect to the annular fixation members, seen along the longitudinal axis of the bone to be corrected. The pin connecting means are therefore preferably arranged outwardly with respect to the ring connecting means, at least are the pin connecting means and the ring connecting means arranged to connect the pins and the annular fixation members such that the pins extend outwardly with respect to the annular fixation members, seen along the longitudinal axis of the bone.

The invention further relates to a method for correcting bones, preferably using a system as mentioned above, the method consisting of a correction phase and a subsequent hardening phase, comprising of:
 connecting at least a first pin to the bone at a first location;
 connecting at least a second pin at a second location at a distance from the first location;
 connecting first and second coupling devices according to the invention to the first and second pins;
 connecting at least a first annular fixation member to the first coupling device and connecting at least a second annular fixation member to the second coupling device;
 correcting the length and/or the orientation of the bone by adjusting the mutual distance and/or the orientation of the annular fixation members during the correction phase;
 connecting a fixator to the first and second coupling devices for fixing the mutual distance between the first and the second pin with the fixation member at least during the hardening phase of the bone;
 removing the annular fixation members from the coupling devices during the hardening phase.

It is possible that the fixator, for instance in the form of a unilateral fixator is already coupled to the coupling device during the correction phase. It is then preferred if the fixator can co-displace freely. In the hardening phase, the fixator can then be fixed for fixing the mutual distance between the annular fixation members. The annular members can then be removed.

It is however preferred if the fixator is connected on completion of the correction phase, wherein after the step of connecting the fixator, the annular fixation members are removed. Before removal of the annular fixation members, the fixator is connected in a load bearing member, such that after connection, the annular fixation members can be removed. The coupling devices according to the invention hereby allow simultaneous connection of the fixator and the annular fixation members.

The present invention is further illustrated by the following Figures, which show preferred embodiments of the coupling device according to the invention, and are not intended to limit the scope of the invention in any way, wherein.

Figure 1:
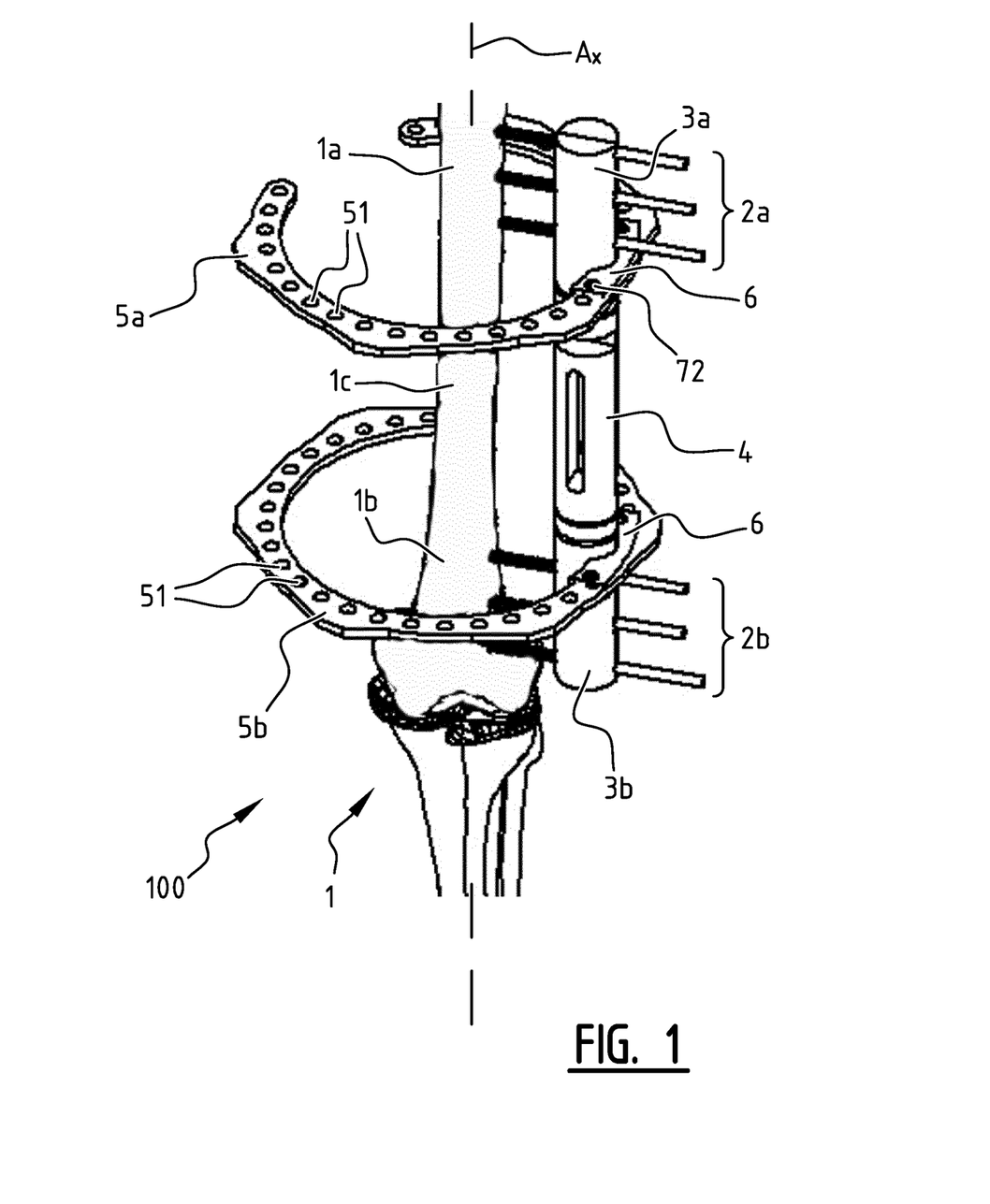
FIG. 1 schematically shows a system for correcting bones with two coupling devices according to the invention.

In FIG. 1, a system 100 for correcting a bone 1 is shown. Three first bone pins 2a are therefore inserted into a first part 1a of the bone 1 and three second bone pins 2b are inserted in a second part 1b of the bone 1, wherein a region to be corrected 1c lies there between.

Coupled to the first and second bone pins 2a, 2b are coupling devices 3a, 3b which are each further arranged to couple to a respective ring shaped fixator, also simply called rings, 5a, 5b and a unilateral fixator 4. Between the rings 5a, b, adjusting means in the form of telescoping tubes can be provided (not shown), which allow the adjustment of the orientation and/or distance of the rings 5a,b and therewith the bone regions 1a, b.

According to the invention, a fixator 4 and a ring 5a,5b can be coupled to a coupling device 3a, 3b at the same time in a load bearing manner. At the same time, the rings 5a,b and the fixator 4 are removably coupled to the coupling devices 3a, 3b such that the fixator 4 or the rings 5a,b can be removed, while the other of the fixator 4 and the rings 5a,b (with adjustment means in between) connect the coupling devices 3a,b in a load bearing manner.

Figure 2:
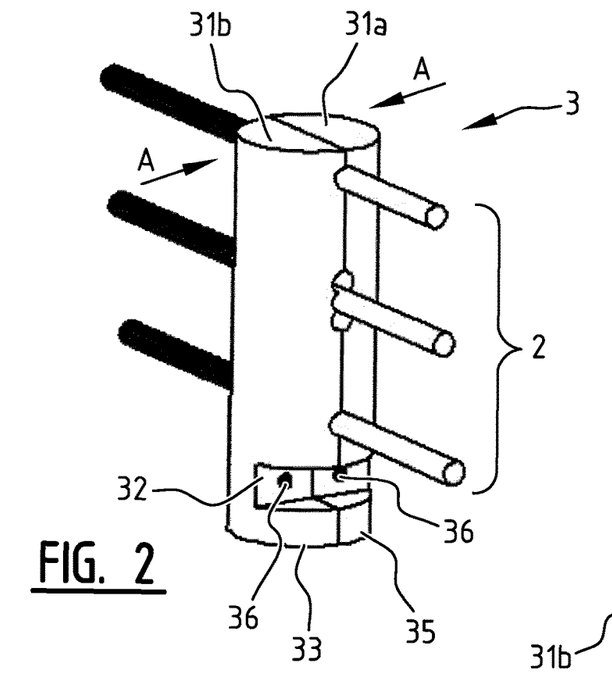
FIGS. 2-4 schematically show a coupling device.
Figure 3:
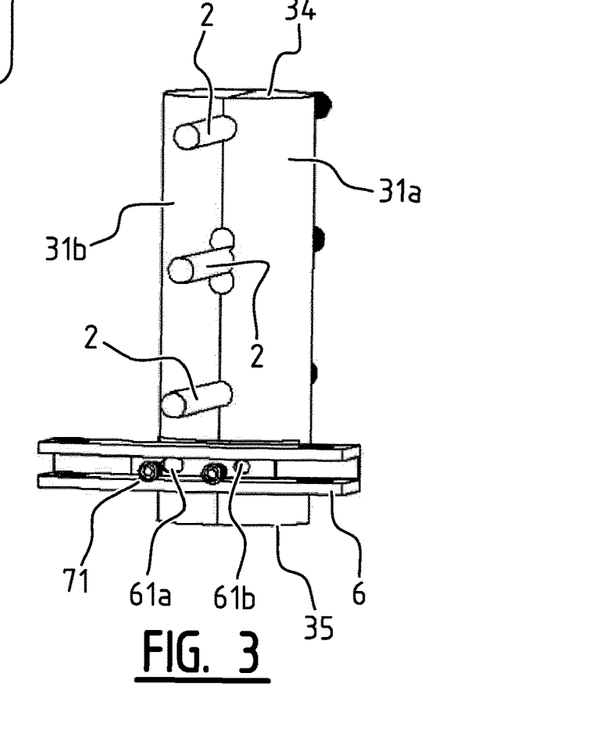

FIGS. 2-3 schematically shows a coupling device, generally indicated with the reference numeral 3. The coupling device 3 has generally cylindrical shape and is formed of two clamping bodies 31a, b. The bodies 31a, b are moveable towards and away from each other to lock the pins 2 in between the bodies 31a, b. The bodies 31a,b are therefore moved in the directions indicated with A. For locking the pins 2, the bodies 31a, b are interlocked with locking means, for instance a screw member (not shown). Each of the parts 31a, b is provided with recesses in order to closely receive the pins 2. The pins 2 are connected to the coupling body near, or towards, a first end 34, whereas on the other end 35, fixator connecting means 33 are provided.

Figure 5:
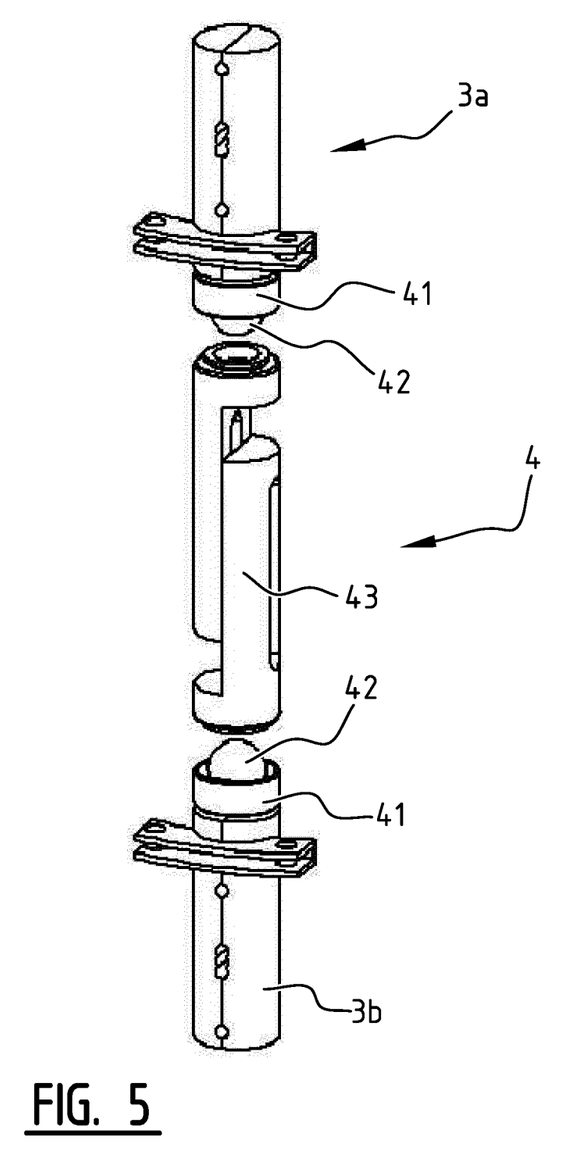
FIG. 5 schematically shows a unilateral fixator in relation to two coupling devices.

With reference to FIG. 5, these fixator connecting means 33 may comprise an as such known bayonet connection to connect to an end part 41 of a unilateral fixator 4. These end parts 41 are connected via a lockable ball joint 42 to the main body 43 of the fixator 4.

Returning to FIGS. 2-4, a groove 32 is provided between the pin connecting means, i.e. the location of connection of the pins, and the fixator connection means 33. This groove 32 is arranged to receive a ring 5 such that a ring can be connected in a compact configuration to the coupling device 3. In the base of the groove 32, two connection holes 36 are provided, each in one clamping body 31a, b.

Figure 4:
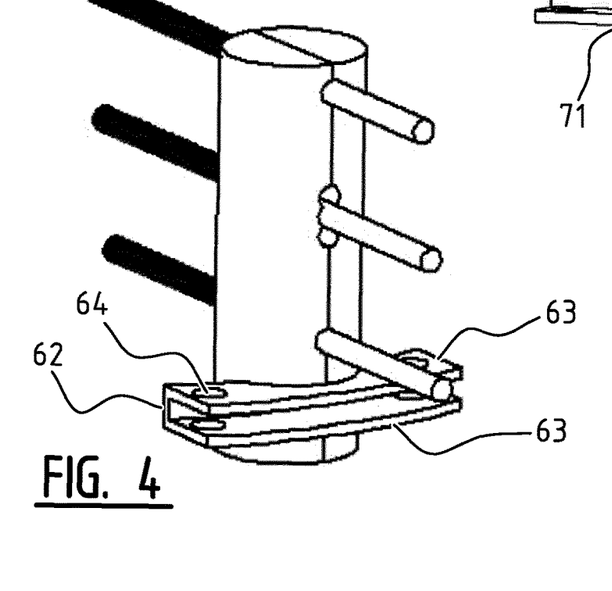

To connect a ring 5 to a coupling device 3, a connecting profile 6 is used. The connecting profile as shown FIGS. 1, 3 and 4 are substantially U-shaped, wherein a base 62 of the U-shape is provided with two connection holes 61a,b, of which one 61a is slot shaped. This allows compensating for any deviations of the positions of the clamping bodies 31a,b due to for instance differing pin thicknesses. The profile 6 is screwed to coupling device 3 using screws 71.

The legs 63 of the U-shape are provided with connection holes 64 which are arranged to cooperate with connection holes 51 of the rings 5. Each leg 63 is provided with two connection holes 64. The rings 5 are again connected to the profile 6 by screwing using screws 72.

Figure 8:
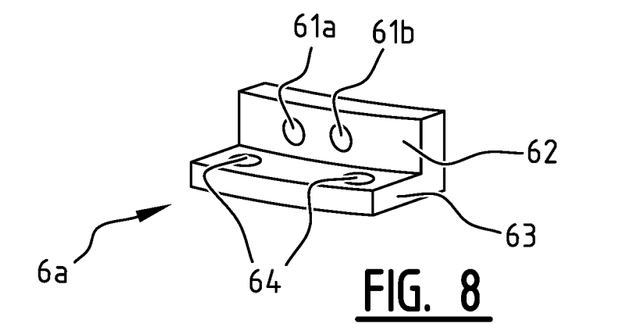
FIG. 8 schematically shows an alternative for a connecting profile.

As an alternative, with reference to FIG. 8, a profile 6a can be used having a L-shaped cross-section. The profile 6a again has a connecting surface 63 extending orthogonally with respect to the surface 62 which is provided with the holes 61a,b for connecting the profile 6a to the coupling device 3.

Figure 6:
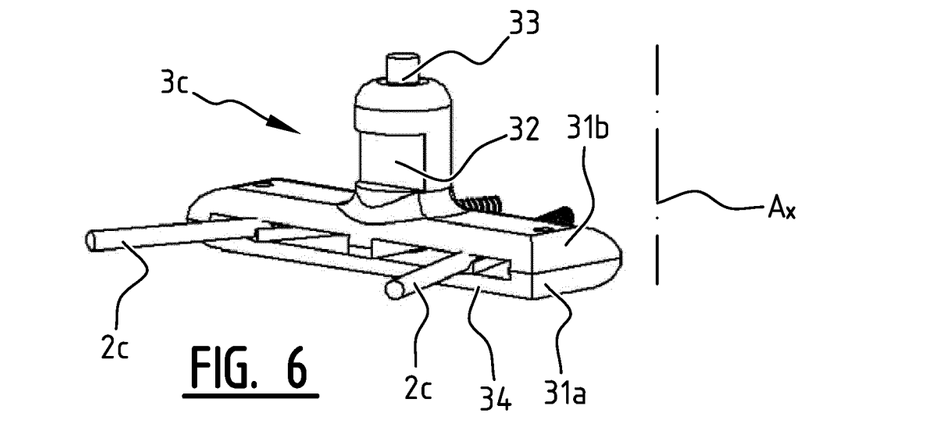
FIGS. 6 and 7 schematically show an alternative embodiment of the coupling device.
Figure 7:
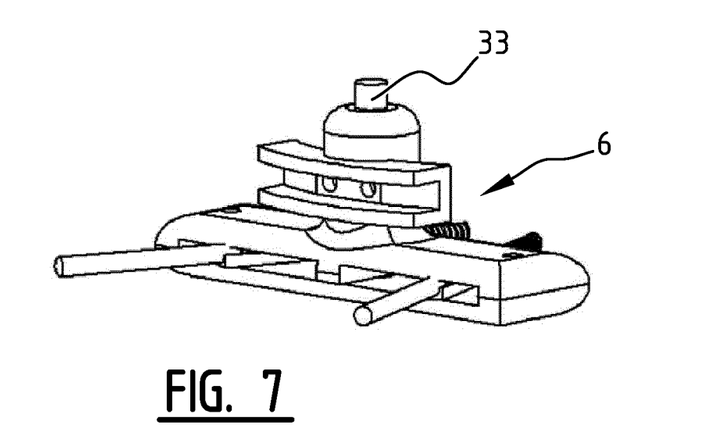

The bone pins 2a, b are orientated along a line parallel to the longitudinal axis Ax of the bone 1. This is however not necessary. As shown in FIGS. 6 and 7, an embodiment of the coupling device 3c is shown arranged to connect to horizontally oriented pins 2c. The coupling device 3c is again provided with two clamping bodies 31a, b which are now movable vertically in order to clamp the pins 2c between the bodies 31a, b. The pins 3c are again connected near an end 34 of the coupling body 3c, whereas the groove 32 for connecting the ring 5, again via a profile 6 as shown in FIG. 7, and the fixator connecting means 33 are located towards the other end of the coupling device 3c.

The present invention is not limited to the embodiment shown, but extends also to other embodiments falling within the scope of the appended claims. It will for instance be appreciated that the annular fixation members or rings do not need to be complete rings. Also semi rings can be used as shown in FIG. 1. It is further possible that the connecting profile 6 is formed integrally with the coupling device.

The invention claimed is:

1. A coupling device for connecting an annular fixation member to a rigid bone pin, wherein the coupling device has an elongated body extending along a straight longitudinal axis from a first end to a second end;

the elongated body comprising a first clamping body part and a second clamping body part moveable towards and away from each other to form a pin connecting means, wherein the pin connecting means is arranged on said elongated body near its first end and arranged for connecting the rigid bone pin to the coupling device, wherein the first clamping body part and the second clamping body part are moveable towards and away from each other to lock a rigid bone pin in between them, and ring connecting means arranged on said elongated body for removably connecting the annular fixation member to the coupling device, wherein the ring connecting means comprise a connecting surface extending in a plane parallel to a plane of the annular fixation member to be connected, wherein the connecting surface is provided with connecting holes which are arranged to connect to holes of the annular fixation member;

wherein the coupling device further comprises fixator connecting means arranged on said elongated body towards its second end and arranged for removably connecting a fixator to the coupling device, wherein the ring connecting means and the fixator connecting means are arranged for simultaneously connecting the annular fixation member and the fixator while the pin connecting means are connected to the rigid bone pin, wherein the ring connecting means are arranged towards the second end of the coupling device.

2. The coupling device according to claim wherein the ring connecting means are arranged to connect the annular fixation member to a side surface of the coupling device.

3. The coupling device according to claim 2, wherein the ring connecting means comprise a groove in the coupling device for receiving the annular fixation member.

4. The coupling device according to claim 1, wherein the connecting surface is part of a connecting profile provided with the connecting holes, wherein the connecting profile is further provided with connection means for connecting the connecting profile to the coupling device.

5. The coupling device according to claim 4, wherein the connecting profile comprises the connecting surface extending in the first plane parallel to the plane of the annular fixation member to be connected, and a second surface under an angle with respect to the connecting surface, wherein the second surface is provided with the connection means for connecting the connecting profile to the coupling device.

6. The coupling device according to claim 4, wherein the connecting profile has a substantially U-shaped cross-section, wherein the legs of the U-shape are shaped to closely receive the annular fixation member there between and wherein the connection means for connecting the connecting profile to the coupling device are provided in the base of the U-shape.

7. The coupling device according to claim 4, wherein the connection means for connecting the connecting profile to the coupling device comprise at least one hole, wherein the coupling device is provided with a coinciding hole for receiving a screw therein.

8. The coupling device according to claim 4, wherein the connection means comprise a first pair of coinciding holes in the connecting profile and the first clamping body part and a second pair of coinciding holes in the connecting profile and the second clamping body part.

9. The coupling device according to claim 8, wherein at least one of the coinciding holes is slot shaped.

10. A system for correcting bones, comprising:
   at least a first rigid bone pin which can be connected to bone at a first location;
   at least a second rigid bone pin which can be connected to bone at a second location at a distance from the first location;
   at least one coupling device comprising:
   pin connecting means coupled to at least the first rigid bone pin;
   ring connecting means and fixator connecting means;
   a unilateral fixator, extending along a longitudinal axis between a first fixator end, which is coupled removably to the fixator connecting means of the coupling device, and a second fixator end, which is coupled to the second rigid bone pin, said unilateral fixator fixing a distance between the rigid bone pins during a hardening phase; and
   at least a first annular fixation member which is removably coupled to the ring connecting means of the coupling device; and
   at least a second annular fixation member which is removably connected to the second rigid bone pin for the purpose of adjusting the bone during a correction phase;
   wherein the ring connecting means comprise a connecting profile provided with connecting holes which are arranged to connect to connection holes of the annular fixation member, wherein the connecting profile is further provided with connection means for connecting the connecting profile to the coupling device;
   wherein the system has at least a configuration with the first and second annular fixation members removed, in which the first rigid bone pin is connected to the bone at the first location, the second rigid bone pin is connected to the bone at the second location, the first and second rigid bone pins being connected via the unilateral fixator, the unilateral fixator being secured to the bone by the first and second rigid bone pins.

11. The system according to claim 10, further comprising a second coupling device coupled to the second rigid pin, wherein the unilateral fixator is coupled removably to the two coupling devices for the purpose of fixing the mutual distance between the rigid pins during the hardening phase, and wherein the second annular fixation member is removably connected to the second coupling device for the purpose of adjusting the bone during the correction phase.

12. The system according to claim 10, wherein said pin connecting means comprise two bodies moveable towards and away from each other to lock a rigid bone pin in between them.

13. A method for correcting bone, consisting of a correction phase and a subsequent hardening phase, comprising:
   connecting at least a first pin to the bone at a first location;
   connecting at least a second pin at a second location at a distance from the first location;
   providing first and second coupling devices, each of said first and the second coupling devices having a single body and comprising fixator connecting means, pin connecting means and ring connecting means directly provided on said single body;
   connecting the pin connecting means of the first coupling device to at least the first pin;
   connecting the pin connecting means of the second coupling device to at least the second pin;
   connecting at least a first annular fixation member to the ring connecting means of the first coupling device and connecting at least a second annular fixation member to the ring connecting means of the second coupling device;
   correcting a length and/or an orientation of the bone by adjusting the mutual distance and/or an orientation of the annular fixation members during the correction phase;
   connecting a unilateral fixator to the fixator connecting means of the first and second coupling devices, wherein said unilateral fixator has an elongated body extending along a straight longitudinal axis and keeps said first and second coupling devices at a distance along said longitudinal axis;
   removing the annular fixation members from the coupling devices during the hardening phase.

14. The method according to claim 13, wherein the step of connecting the unilateral fixator is subsequent to the correction phase, wherein after the step of connecting the unilateral fixator, the annular fixation members are removed.

* * * * *